US005642730A

United States Patent [19]
Baran

[11] Patent Number: 5,642,730
[45] Date of Patent: Jul. 1, 1997

[54] CATHETER SYSTEM FOR DELIVERY OF AEROSOLIZED MEDICINE FOR USE WITH PRESSURIZED PROPELLANT CANISTER

[75] Inventor: George Baran, Ontario, Canada

[73] Assignee: Trudell Medical Limited, Canada

[21] Appl. No.: 261,490

[22] Filed: Jun. 17, 1994

[51] Int. Cl.$^6$ ............................................. A61M 16/00
[52] U.S. Cl. ........................... 128/207.14; 128/200.26; 128/207.15; 128/203.12; 128/200.23
[58] Field of Search .................... 128/200.26, 207.14, 128/207.15, 207.16, 200.18, 200.21, 200.23, 203.12; 604/171

[56] References Cited

U.S. PATENT DOCUMENTS

| 829,952 | 9/1906 | Dean | 604/275 |
|---|---|---|---|
| 852,154 | 4/1907 | Bariffi | 604/275 |
| 4,270,530 | 6/1981 | Baum et al. | |
| 4,584,998 | 4/1986 | McGrail | |
| 4,622,968 | 11/1986 | Persson | 128/200.26 |

(List continued on next page.)

FOREIGN PATENT DOCUMENTS

| 0 289 336 A2 | 2/1988 | European Pat. Off. |
| 0 587 380 A1 | 3/1994 | European Pat. Off. |
| 0 180 038 A1 | 9/1985 | Germany |
| WO89/05670 | 6/1989 | WIPO |
| WO93/17744 | 9/1993 | WIPO |

OTHER PUBLICATIONS

Carlton, Graziano C.; Barker, Robert L.; Benua, Richard S.; Guy, Yvonne G; Airway Humidification With High-Frequency Jet Ventilation. *Critical Care Medicine*, vol. 13, No. 2, (1985).

Aiache, Jean-Marc; The Ideal Drug Delivery System: A Look into the Future. *Journal of Aerosol Medicine*, vol. 4, No. 4, 1991.

Wheeldon, Walker, Murphy, and Turner; Aerosolized Endotoxin in Animals, (1992).

Jager-Waldau, Reinhold; A Two-Phase-Flow Mechanical Spray Pump: A Possible Alternative To Propellant Driven MDIs. *Journal of Biopharmaceutical Sciences*, 3(1/2), 077-084, (1992).

Niven, Ralph W.; Kacmarek, Robert M.; Brain, Joseph D.; Peterfreund, Robert A.; Small Bore Nozzle Extensions to Improve the Delivery Efficiency of Drugs from Metered Dose Inhalers: Laboratory Evaluation. *Am Rev Respir Dis*, vol. 147. pp. 1590-1594, 1993.

Hoover, Mark D.; Harkema, Jack R.; Muggenburg, Bruce A.; Spoo, Jerry W.; Gerde, Per; Staller, Heather J.; Hotchkiss, Jon A. A Microspray Nozzle for Local Administration of Liquids or Suspensions to Lung Airways via Bronchoscopy. *Journal of Aerosol Medicine*, vol. 6, No. 2, 1993.

(List continued on next page.)

*Primary Examiner*—V. Millin
*Assistant Examiner*—William J. Deane, Jr.
*Attorney, Agent, or Firm*—Brinks Hofer Gilson & Lione

[57] ABSTRACT

An improved system for delivery of an aerosolized medicine to a patient's respiratory system. The system uses a pressurized canister that contains a mixture of a medicine and a propellant which may be in a liquid state. The canister has an outlet from which the mixture can exit. The system includes an extension catheter that connects at a proximal end to the outlet of the canister. The extension catheter has a length such that a distal end can be positioned either in an endotracheal tube or deep in the respiratory tract of the patient while the proximal end of the extension catheter is connected to the canister which is located outside the patient's body. The extension catheter includes at least one lumen extending therethrough for conveying the medicine and liquid propellant mixture from the canister to a distal exit orifice where an aerosol can be generated as the propellant evaporates. The aerosolized medicine is carried by the patient's inhalation and delivered to the lungs. The extension catheter may be positioned in an endotracheal tube or alternatively may be used with a patient who is not intubated.

26 Claims, 7 Drawing Sheets

U.S. PATENT DOCUMENTS

| | | |
|---|---|---|
| 4,655,746 | 4/1987 | Daniels et al. . |
| 4,669,463 | 6/1987 | McConnell . |
| 4,739,756 | 4/1988 | Horn . |
| 4,819,664 | 4/1989 | Nazari ................................ 128/207.15 |
| 4,821,714 | 4/1989 | Smelser . |
| 4,829,996 | 5/1989 | Noakes et al. . |
| 4,832,012 | 5/1989 | Raabe et al. . |
| 4,840,172 | 6/1989 | Augustine et al. ................ 128/207.14 |
| 4,881,542 | 11/1989 | Schmidt et al. ................... 128/207.14 |
| 4,945,929 | 8/1990 | Egilmex . |
| 4,955,375 | 9/1990 | Martinez . |
| 5,025,806 | 6/1991 | Palmer et al. . |
| 5,031,613 | 7/1991 | Smith et al. . |
| 5,049,137 | 9/1991 | Thompson . |
| 5,060,646 | 10/1991 | Page . |
| 5,062,423 | 11/1991 | Matson et al. . |
| 5,078,131 | 1/1992 | Foley . |
| 5,115,971 | 5/1992 | Greenspan et al. . |
| 5,125,893 | 6/1992 | Dryden . |
| 5,146,916 | 9/1992 | Catalani . |
| 5,167,622 | 12/1992 | Muto . |
| 5,186,166 | 2/1993 | Riggs et al. . |
| 5,186,167 | 2/1993 | Kolobow ............................ 128/207.14 |
| 5,207,220 | 5/1993 | Long . |
| 5,231,983 | 8/1993 | Matson et al. . |
| 5,233,979 | 8/1993 | Strickland . |
| 5,285,778 | 2/1994 | Mackin ............................. 128/200.26 |
| 5,287,849 | 2/1994 | Piper et al. . |

OTHER PUBLICATIONS

Taylor, Robert H.; Lerman, Jerrold; Chambers, Carole; Dolovich, Myrna; Dosing Efficiency and Particle–Size Characteristics of Pressurized Metered–Dose Inhaler Aerosols in Narrow Catheters. Presented at Annual Meeting American Society of Anesthesiologist, Las Vegas, Oct., 1990.

Hess, Dean; Inhaled Bronchodilators During Mechanical Ventilation: Delivery Techniques, Evaluation of Response, and Cost Effectiveness. *Respiratory Care*, vol. 39 No. 2, Feb., 1994.

Judson, Marc A.; Sahan, Steven A.; Mobilization of Secretions in ICU Patients. *Respiratory Care*, vol. 39 No. 3, Mar., 1994.

CATHETER SYSTEM FOR DELIVERY OF AEROSOLIZED MEDICINE FOR USE WITH PRESSURIZED PROPELLANT CANISTER

REFERENCE TO RELATED APPLICATION

The present application incorporates by reference the copending application entitled "Nebulizing Catheter System and Methods of Use and Manufacture" filed by the same inventor of the present application and on even date herewith and assigned Ser. No. 08/261,866.

BACKGROUND OF THE INVENTION

The present invention relates to the delivery of medication to the lungs and more particularly, the present invention relates to a delivery system for the application of an aerosolized medication to the lungs or to a specific region within the lungs with improved delivery rates, efficiencies, and control.

Many types of medication can be administered to a patient via the respiratory tract. Medication delivered through the respiratory tract may be carried with a patient's inhalation breath as airborne particles (e.g. an aerosol or nebula) into the lungs where the medication can cross through the thin membrane of the lungs and enter the patient's bloodstream. Delivery of medication via the respiratory tract is preferred in many circumstances because medication delivered this way enters the bloodstream very rapidly. Delivery of medication to the lungs may also be preferred when the medication is used in a treatment of a disease or condition affecting the lungs in order to apply or target the medication as close as physically possible to the diseased area.

Although delivery of medication via the respiratory tract has been used for delivery of medications for many years, there are difficulties associated with such prior systems that have limited their use and application. For example, conventional methods have provided for only limited medication delivery rates, efficiency, and control. Conventional methods for aerosol delivery result in a substantial portion of the medicine failing to be delivered to the lungs, and thereby possibly being wasted, or possibly being delivered to other parts of the body, e.g. the trachea.

Aerosols in general are relatively short-lived and can settle out into larger particles or droplets relatively quickly. Aerosols can also impact each other or other objects, settle out as sediment, diffuse, or coalesce. Aerosol particles can also be subject to hydroscopic growth as they travel. Delivery of medicine as airborne particles requires conversion of the medicine, which may be in liquid form, to an aerosol followed relatively quickly by application of the aerosol to the respiratory tract. One such device that has been utilized for this purpose is an inhaler. Inhalers may atomize a liquid to form an aerosol which a person inhales via the mouth or nose. Inhalers typically provide only limited delivery of medication to the alveoli of the lungs since much of the medication is deposited on the linings of the respiratory tract. It is estimated that as little as 10–15% of an aerosol inhaled in this way reaches the alveoli.

Aerosol delivery of a medication to a patient's respiratory tract also may be performed while the patient is intubated, i.e. when an endotracheal tube is positioned in the patient's trachea to assist in breathing. When an endotracheal tube is positioned in a patient, a proximal end of the endotracheal tube may be connected to a mechanical ventilator and the distal end is located in the trachea. An aerosol may be added to the airflow in the ventilator circuit, conveyed to the endotracheal tube, and carried by the patient's inhalation to the lungs. A significant amount of the aerosolized medication may be deposited inside the endotracheal tube and the delivery rate of the medicine to the lungs is also relatively low and unpredictable.

The low and unpredictable delivery rates of prior aerosol delivery systems have limited the types of medications that are delivered via the respiratory tract. For new medications that are relatively expensive, the amount of wasted medicine may be a significant cost factor in the price of the therapy. Therefore, it would be advantageous to increase the delivery rate or efficiency of a medicine delivered to the lungs.

It may also be advantageous to be able to target medication to a specific bronchus, or specific groups of bronchia, as desired, while avoiding delivery of medication to other portions of the lungs.

Another consideration is that some medications or other agents that can be delivered as aerosols can have adverse side effects. Therefore, it would be advantageous to minimize the overall amount of medication or agent delivered while maintaining the efficacy of the medication by providing the same or a greater amount of the medication to the desired treatment site.

Taking into account these and other considerations, it would be advantageous to improve the delivery rate and efficiency of aerosolized medicines delivery via the respiratory tract.

SUMMARY OF THE INVENTION

According to a first aspect of the present invention, there are provided an improved system and method for delivery of an aerosolized medicine to a patient's respiratory system. The system uses a pressurized canister that contains a mixture of fine particles of a medicine and a propellant which may be in a liquid state. The canister has an outlet from which the mixture can exit. The system includes an extension catheter that connects at a proximal end to the outlet of the canister. The extension catheter has a length such that a distal end can be positioned either in an endotracheal tube or deep in the respiratory tract of the patient while the proximal end of the extension catheter is connected to the canister which is located outside the patient's body. The extension catheter includes at least one lumen extending therethrough for conveying the medicine/propellant mixture from the canister to a distal exit orifice where an aerosol can be generated as the propellant evaporates. The aerosolized medicine is carried by the patient's inhalation and delivered to the lungs. The extension catheter may be positioned in an endotracheal tube or alternatively may be used with a patient who is not intubated.

Throughout this specification and these claims, the extension catheter is described as used for the delivery of medicine or medication. It is intended that the terms "medication", "medicine", and "drug" be understood to include other agents that can be delivered to the lungs for diagnostic or therapeutic purposes, such as tracers. In addition, although the extension catheter is discussed as being placed in the trachea, it should be understood that unless otherwise noted the extension catheter can be positioned in any airway of the respiratory tract.

BRIEF DESCRIPTION OF THE DRAWINGS

FIG. 1 is a plan view of an embodiment of the present invention shown in place in the trachea of a patient who is intubated.

FIG. 2 is an alternate embodiment of the invention shown in FIG. 1.

DETAILED DESCRIPTION OF THE PRESENTLY PREFERRED EMBODIMENTS

Figure 1:
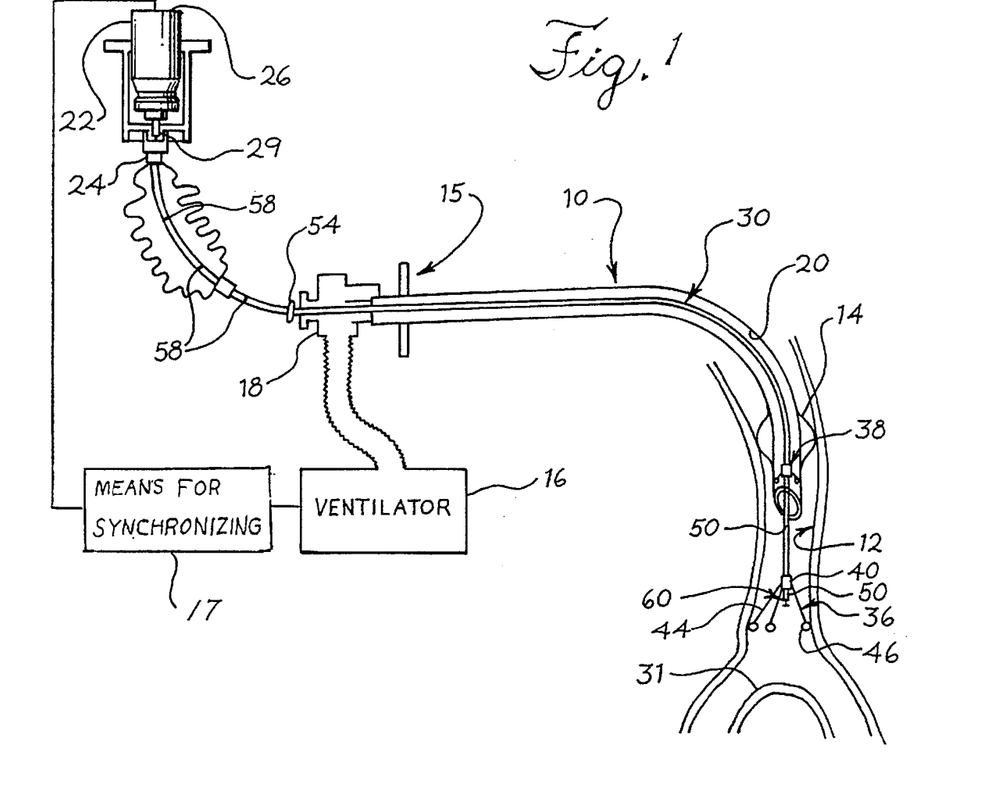

Referring to FIG. 1, there is depicted a first embodiment of the present invention. An endotracheal tube 10 is positioned in a patient's respiratory system 12. The endotracheal tube may be of a conventional type or may be specially designed for use with the present invention, as described in more detail below. The endotracheal tube may have an inflatable cuff or balloon 14 located close to its distal end. A proximal end 15 of the endotracheal tube is connected to a ventilator 16 which may also have a conventional construction. The ventilator 16 connects to the proximal end of the endotracheal tube 10 by means of a manifold fitting 18. The manifold 18 is adapted to provide a connection between the ventilator 16 and the endotracheal tube 10, and in addition, the manifold 18 permits the introduction of a separate catheter into a main ventilation lumen 20 of the endotracheal tube 10. The manifold 18 may be of the type disclosed in U.S. Pat. No. 5,078,131 (Foley), the entire disclosure of which is incorporated herein by reference.

At a location outside of the endotracheal tube 10 and external of the patient's respiratory system 12 is a pressurized canister 22. The canister 22 contains a volume of medicine mixed with a propellant. The medicine may be in fine particle form or may be in a liquid form mixed with the liquid propellant. The canister retains the medicine/propellant mixture under pressure in order to generate an aerosol of the medicine when the medicine/propellant mixture is expelled from the canister 22 to ambient pressure. The canister 22 includes an outlet 24 from which the medicine/propellant mixture can exit. The canister 22 should be suitably designed to withstand the pressure. The canister 22 is preferably a closed can that is filled with medicine and propellant, pressurized and then sealed during the manufacture of the canister.

In a preferred embodiment, the canister 22 may be similar or identical to the type of canister used in a conventional MDI (metered dose inhaler). An MDI has an actuator mechanism that uses a pressurized canister as a component. The canister contains a medicine/propellant mixture that is sealed under pressure. The MDI expels an aerosol in measured dosages from the canister to an outlet suitably designed to conform to a patient's mouth. The type of canister used in conjunction with embodiments of the present invention may differ in some respect from those used in MDI devices since the present embodiments may be suitable for delivering a wider variety of medicines than is possible with MDI devices.

Figure 3:
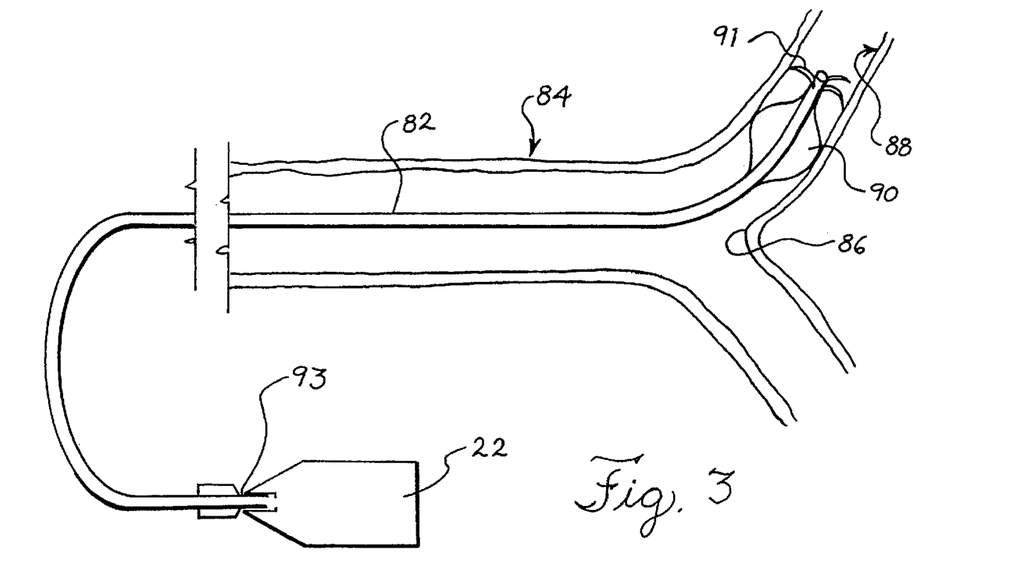
FIG. 3 is a plan view of another embodiment of the present invention of FIGS. 1 and 2 shown in place in the trachea of a patient who is not intubated.

Connected to the outlet 24 of the canister is an extension catheter 30. The extension catheter 30 extends from the canister 22 through the manifold 18 and into the endotracheal tube 10. In the embodiment shown in FIG. 1, the extension catheter 30 extends through the main ventilation lumen 20 of the endotracheal tube 10 and out the distal end thereof. The extension catheter 30 may be permanently attached to the canister 22 during manufacture or alternatively the extension catheter may have a proximal connector 29 that is matable with an exit nozzle of the canister 22 and to which the extension catheter may be releasibly connected. If the extension catheter includes a proximal connector 29, actuation of the canister 22 may be provided by pushing the proximal end of the extension catheter toward the nozzle. In a present embodiment, the extension catheter 30 In a present embodiment, the extension catheter 30 has a length such that a proximal end can be attached to the pressurized canister 22 while the distal end extends beyond the distal end of the endotracheal tube by approximately 1–7 centimeters. Alternatively, the distal end of the extension catheter may be located proximal of the distal end of the endotracheal tube inside the ventilation lumen of the endotracheal tube, or alternatively, the distal end of the extension catheter may be aligned with the distal end of the endotracheal tube. If it is desired to deliver medicine selectively into one of the bronchi, the distal end of the extension catheter 30 may be positioned past the carina 31, as illustrated in FIG. 3. The distal end of the extension catheter 30 may even be positioned deep inside the bronchia of the lungs. Alternatively, the extension catheter may also be used in the nasal passages and accordingly the length may be correspondingly shorter. The extension catheter may also be positioned through the nasal passages instead of the mouth.

The extension catheter 30 has a lumen through which the medicine/propellant mixture flows from the pressurized canister to at least one distally located exit orifice. In a present embodiment, the extension catheter 30 has an O.D. of 0.035 to 0.092 inches and a wall thickness of approximately 0.007 inches. The small size of the extension catheter 30 provides for maintaining the medicine/propellant mixture under pressure while it flows through the extension catheter. The medicine/propellant mixture is preferably maintained under pressure until it reaches the distal end of the extension catheter, and accordingly the extension catheter may have a uniform profile along its length, or alternatively may taper slightly or have a narrow distal orifice to maintain pressure through the lumen although some evaporation of the propellant in the extension catheter lumen may occur. In addition, because the extension catheter has a relatively small exterior size, it does not impede the ventilating function provided by the endotracheal tube into which it is positioned so that the extension catheter may be left in the endotracheal tube for extended periods of time. The embodiments of the extension catheter described herein may be used with canisters that have the capability of generating a variety of aerosol particle distributions. The output flow rate and aerosol particle size distribution of the extension catheter of FIG. 1 would be a function largely of the design of the pressurized canister.

A significant advantage provided by the extension catheter 30 is that the aerosol produced by the expansion of the medicine/propellant mixture and evaporation of the propellant occurs at a location deep within the trachea or even in the bronchi of the lungs. This reduces losses due to impaction of the aerosol on the trachea walls, on the endotracheal tube wall, or in the ventilator circuit of an external ventilator. This may have the advantage of reducing the overall amount of medicine delivered and increasing the portion of medicine delivered to the desired location thereby resulting in less waste. Also, where it is desired to minimize the total amount of medicine delivered, for reasons of toxicity for example, use of the extension catheter can maintain a desired level of efficacy while reducing the overall amount of medicine or other agent delivered.

Appropriate centering and aiming of the extension catheter can be an important factor affected the delivery rate. In order to facilitate positioning, the extension catheter is preferably constructed with sufficient torsional rigidity so that rotation of the proximal end results in approximately a one-to-one responsive movement at the distal end. Centering and aiming of the extension catheter are related to anatomical factors. In some circumstances, it is preferable to position the distal tip of the extension catheter into either the left, right or both branches of the lungs. Positioning of the tip closer to the alveoli of the lungs may enhance drug delivery efficiency. With the extension catheter 30 of FIG. 1, the aerosolized medicine can be delivered to either bronchus of the lungs and further can be directed into specific airway passages of either lung for selective aerosol delivery (as illustrated in FIG. 3).

In addition to the factors mentioned above, proper location, orientation, and alignment of the extension catheter in the patient's anatomy can also be affect the efficiency and delivery of the aerosolized medicine. Efficiency may be enhanced if aerosolized medicine avoids impaction on the walls of the trachea or the endotracheal tube, if one present. In general, it is preferable to align the extension catheter with respect to the airway passage. Also, it is generally desirable to allow the aerosolized particles to avoid impaction for several centimeters after being expelled from the distal end of the extension catheter so that the particles can lose velocity and become entrained in the inspiratory airflow.

The embodiment of FIG. 1 provides for alignment of an extension catheter in a patient's respiratory system. Located around a distal portion of the extension catheter 30 are one or more centering devices. In a preferred embodiment, there are two centering devices. Specifically, a first centering apparatus 36 is located on the shaft of the extension catheter 30 close to the distal end thereof. In a present embodiment, the first centering device 36 is less than approximately 1 cm from the distal end. A second centering device 38 is located axially along the extension catheter shaft proximally from the first centering device 36. In a present embodiment, the two centering devices are approximately 0.5 to 3 inches apart. The two centering devices not only serve to position the extension catheter centrally in the trachea, but also serve to align the distal tip of the extension catheter to expel the nebulate plume along a central axis of the trachea. The centering devices may be constructed similar to the device disclosed in U.S. Pat. No. 5,078,131 (Foley).

The first centering apparatus 36 includes a retainer ring 40 fixed to the shaft of the extension catheter and a plurality of arms 44 connected to the ring 40. In a preferred embodiment, there are three arms 44. Located at the end of each of the arms 44 opposite its connection to the ring 40 is a ball 46. In one embodiment, the arms 44 are flexible and resilient and may be composed of a superelastic material such as nitinol or a spring tempered metal or a suitable plastic so that they will spring outward against the walls of the trachea to center the extension catheter. In a preferred embodiment, the arms are formed of a thin resilient wire or polymer, preferably less than approximately 0.015 inches in diameter. Alternatively, the arms and/or the balls may be made of a radiopaque material or coated with a radiopaque material. In this embodiment, the second centering device 38 may be the similar to the first centering device 36. It is an advantage of the first centering device 36 that the arms 44 are located somewhat in advance of the distal end of the extension catheter. This positions the arms 44 in the portion of the trachea into which the aerosol will be initially flowing. Thus, the centering device orients the distal tip of the extension catheter relative to the portion of the trachea beyond the distal tip thereby helping to reduce impaction along this portion.

The extension catheter 30 may be provided with radiopaque markings 50 to facilitate positioning and placement. The radiopaque markings 50 may be provided by radiopaque bands of metal or heat shrunk bands of doped radiopaque plastic that are attached to the extension catheter shaft, or alternatively the markings 50 may be provided by doping the plastic material of the extension catheter shaft with a radiopaque material. The markings 50 may be graduated to facilitate recognition, or alternatively may extend over a portion or all of the extension catheter. Alternatively, the markings may be designed for ultrasonic detection and may be provided by an ultrasonically observable material or texture in the distal tip. In addition, the extension catheter may have a stripe, which may be radiopaque or ultrasonically visible, to help ascertain the rotational position of the distal end of the extension catheter. The stripe may be formed by a co-extrusion process during formation of the catheter or by embedding a wire in the catheter shaft wall.

The extension catheter may also include a user-adjustable safety stop 54 located along a proximal portion that engages a proximal portion of the endotracheal tube or the fitting 18. The safety stop 54 ensures that the distal end of the extension catheter 30 is correctly positioned with respect to the distal end of the endotracheal tube 10 and prevents the distal end of the extension catheter from extending too far into the trachea. In addition to the safety stop 54, the proximal portion of the extension catheter 30 may also include graduated markings 58 that would be visible to the physician handling the proximal end of the extension catheter to enable a determination of the position of the distal end of the catheter 30 relative to a distal end of the endotracheal tube 10.

The extension catheter is preferably constructed of a biocompatible, chemically resistant polymer in order that it is suitable for use with a wide variety of drugs. The catheter shaft is preferably composed of a clear tubing to allow visualization of contaminants or blockages of the interior lumens. In a present embodiment, the catheter shaft is composed of polyethylene or nylon tubing. The extension catheter shaft preferably has a low friction surface. The polymer tubing is preferably exposed to high energy radiation to crosslink the polymer molecules to provide for favorable material properties, such as the ability to maintain orifice dimensions and tolerances during the forming process. During the manufacturing process, the extension catheter may be pre-sterilized by means of a conventional process, such as a gamma ray or electron beam. The extension catheter may be disposable after use or may be reusable to a limited extent if appropriate means are used to maintain sterility, e.g. a sheath.

The embodiment of FIG. 1 may be deployed by first positioning the endotracheal tube 10 in the respiratory tract 12 of the patient. This may be performed in a conventional manner. Next, the extension catheter 30 is inserted into the endotracheal tube. The extension catheter 30 including the centering apparatus is advanced through a port on the fitting 18 and into the ventilation lumen 20 of the endotracheal tube 10. The arms 44 of the centering devices 36 and 38 are formed so that they assume a size larger than the diameter of the trachea and/or ventilation lumen 20. The distal end of the catheter 30 is advanced out the distal end of the endotracheal tube 10. When the balls 46 are advanced out the endotracheal tube 10, they spring out to an expanded size and engage the walls of the trachea. The balls 46 provide a relatively smooth surface to limit irritation or injury to the trachea walls. The proximal end of the extension catheter 30 is connected to the pressurized canister 22. The canister 22 is operated either manually or automatically to discharge an aerosol of medicine through the lumen of the extension catheter 30. The canister is operated by pushing the extension catheter in a proximal direction toward the nozzle of the canister. Preferably, the canister 22 is operated in coordination with the patient's breathing so that the aerosol is carried by the patient's inhalation to the lungs. The aerosolized medicine exits the extension catheter 30 out an orifice 60 located at a distal end of the extension catheter. With the arms 44 of the centering device 36 expanded, the extension catheter 30 is centered in the trachea so that the aerosol discharged from the distal orifice 60 of the extension catheter has minimal contact with the walls of the trachea.

In the preferred embodiment of FIG. 1, the extension catheter 30 is removable from, and replaceable with respect to, the endotracheal tube 10. This provides several significant advantages. First, the extension catheter 30 may be specifically designed and chosen to have the desired operating characteristics suitable for delivery of the particular medication being administered to the patient. In addition, the fact that the extension catheter 30 is removable and replaceable provides versatility and flexibility regarding the therapy and dosage regime that can be chosen by the physician. For example, a decision by the physician whether to deliver a medication to the respiratory tract, and the selection of the type and dosage of the medication to be delivered, need not be made by the physician until after the endotracheal tube is already in place in the patient. When the physician determines the proper type of medication to the delivered to the patient via the respiratory tract, the appropriate canister 22 and extension catheter 30 can be selected and inserted into the endotracheal tube 10. Further, the extension catheter 30 can be removed after it is used and therefore it is not necessary for the extension catheter to be left in the patient and occupy space in the patient's respiratory tract or in the endotracheal tube 10 when it is no longer needed. When it is necessary to remove the extension catheter 30, it can be withdrawn in a proximal direction back out of the endotracheal tube 10. In addition, the decision regarding the proper type of medication can be revisited again at a later time. If a different type of canister or extension catheter is required, the endotracheal tube need not be replaced as well.

To facilitate removal and reinsertion of the extension catheter, the extension catheter may be provided with a flexible storage sheath 61. The flexible storage sheath 61 may be similar to the type of storage sheaths used in conjunction with suction catheters. The storage sheath 61 is connected at a proximal end to the fitting by which the extension catheter 30 connects to the canister 22 and at a distal end to another fitting that can slide along the shaft of the extension catheter. The distal fitting of the sheath 61 connects to the port on the proximal end of the endotracheal tube 10. The storage sheath 61 is used to receive the extension catheter 30 when it is being withdrawn from the endotracheal tube 10. The storage sheath 61 is sealed and can maintain the withdrawn extension catheter in a sterile condition when it is temporarily removed from the patient's respiratory system. The storage sheath 61 also allows the physician to re-insert the extension catheter into the patient. In this manner, the extension catheter can be reinserted and used again with respect to a patient and can be maintained in a sterile condition while withdrawn from the patient.

It is generally considered preferable to operate the catheter so as to generate an aerosol that is carried by a patient's inhalation to the lungs. This requires a pulsing of the aerosol generation so that it is timed to coincide with the inhalation of the patient. If the patient is intubated, the timing of the nebulization can be synchronized with the operation of the ventilator. It is recognized that it may be preferable to begin the nebulization slightly in advance of, at, or slightly after, the beginning of the inhalation period in order to account for the distance between the nebulization tip and the alveoli. Also, it may be preferable to stop the nebulization slightly before the end of the inhalation period in order to avoid wasting aerosol after the inhalation flow has stopped. A means 17 for synchronizing operation of the catheter to generate an aerosol may be provided as shown in FIG. 1.

Figure 2:
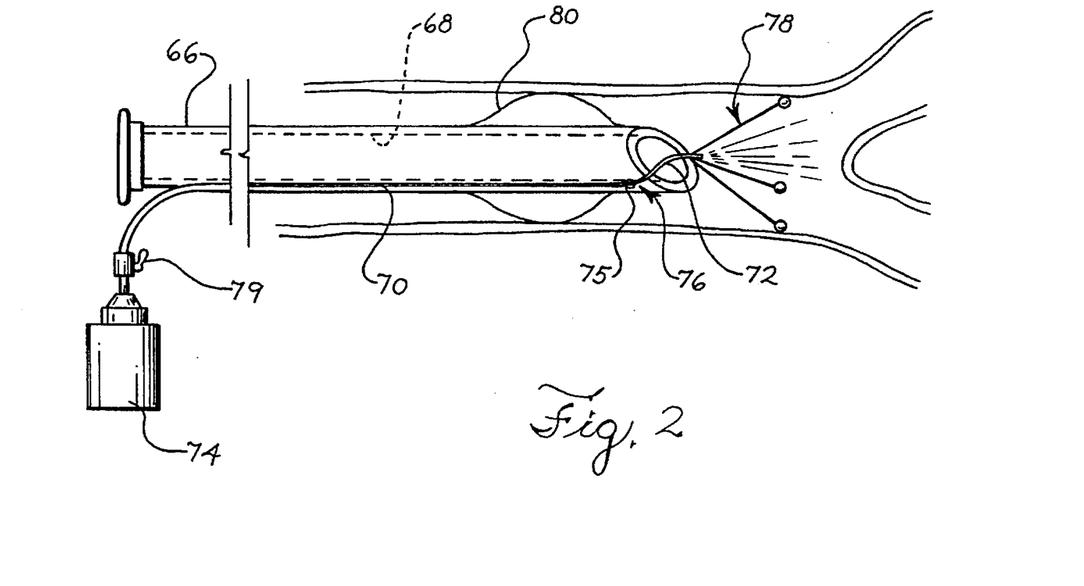

Referring to FIG. 2, there is shown another embodiment of the present invention. An endotracheal tube 66 has a main ventilation lumen 68 and an auxiliary lumen 70. The auxiliary lumen 70 is sized and adapted to receive a catheter extension 72 that connects to an outlet of a pressurized canister 74. The pressurized canister 74 and the catheter extension 72 may be similar or identical to those of FIG. 1. In this embodiment, the auxiliary lumen 70 in the endotracheal tube 66 may facilitate placement and alignment of the extension catheter 72 at a distal end of the endotracheal tube. The auxiliary lumen 70 terminates distally in an opening 75 at a location 76 where the auxiliary lumen 70 merges into the main lumen 68 of the endotracheal tube 66. This location 76 is close to the distal end of the endotracheal tube and in one embodiment is approximately 5 cm from the distal end.

In order to facilitate alignment of the extension catheter 72, a centering device 78 may be provided. The centering device 78 may be similar to the centering device 36 shown in FIG. 1. In an alternative embodiment, the centering device may include wings instead of arms as in FIG. 2. Alternatively, the centering device 78 may be associated with and connected to the endotracheal tube 66 instead of the extension catheter 72. In another alternative, the function of the centering device 78 may be provided by imparting a predetermined curvature to the shape of the distal end of the extension catheter so that it assumes the predetermined curvature when it exits the distal opening 75 so that the extension catheter would not need to have wings or arms. In a further alternative, the endotracheal tube could be provided with a predetermined distal curvature which is used to aim the extension catheter.

In the embodiment of FIG. 2, the extension catheter 72 is shown with its distal tip extending distally of the distal end of the endotracheal tube 66. However, in alternative embodiments, the distal end of the extension catheter 72 may be located proximally of the distal end of the endotracheal tube 66 inside the main ventilation lumen 68, or alternatively, the distal end of the extension catheter 72 may be aligned with the distal end of the endotracheal tube.

Instead of using a proximal centering device, as in FIG. 1, in the embodiment of FIG. 2 the function of the proximal centering device is provided by the endotracheal tube 66. To enhance this centering function, the endotracheal tube may incorporate a distal, elongated occlusion cuff or balloon 80 to co-axially align it in the trachea. Most conventional endotracheal tubes are provided with a curvature to facilitate positioning the trachea of a patient. In addition, most conventional endotracheal tubes are relatively stiff. These factors may result in the misalignment of the distal end of the endotracheal tube relative to a patient's trachea. In order to use the endotracheal tube for centering of the extension catheter, it may be preferable to make the tip of the endotracheal tube 66 straighter and/or more flexible than in conventional endotracheal tubes to ensure proper concentricity with the occlusion balloon and the trachea.

The extension catheter 72 is preferably removable from the auxiliary lumen 70 of the endotracheal tube 66, however in alternative embodiments, the extension catheter may be formed to be non-removable from the tube 66 or may be formed to be part of the tube 66.

In the embodiment of FIG. 2, the extension catheter 72 is also includes a manual valve mechanism 79, such as a stop cock, located in line with the canister 22 in a proximal portion of the extension catheter. The manual valve mechanism 79 serves to shut off the flow of propellant-medicine in the flow lumen of the extension catheter. In an alternative embodiment, the proximal end of the extension catheter has a self-sealing port, e.g. a closure valve, that prevents access to the lumen of the extension catheter when it is not engaged in the canister 22.

In the embodiments of the invention shown in FIGS. 1 and 2, the extension catheter 30, 72 is shown used in conjunction with an endotracheal tube either of a conventional type 10, as in FIG. 1 or of a type especially designed for use with the extension catheter such as the endotracheal tube 66 of FIG. 2. As shown in FIG. 3, an extension catheter 82 according to another embodiment of the present invention may also be used without a separate endotracheal tube, i.e. the extension catheter may be used with a patient who is not intubated. In FIG. 3, the extension catheter 82 is positioned in the respiratory system 84 of a patient directed past the carina 86 into one of the bronchi 88 of the lungs. In order to facilitate centering the extension catheter 82, it is provided with an inflatable cuff 90. The inflatable cuff 90 connects via a lumen of the extension catheter shaft to a inflation source (not shown) located at a proximal end of the extension catheter. The inflation source may be similar to those used for endotracheal tube cuffs. The inflatable cuff 90 on the extension catheter 82 also allows the extension catheter 82 to be used for selective airway medicine delivery. In addition to the inflatable cuff 90, the extension catheter 82 may also have a centering device 91 similar to the centering device of FIGS. 1 and 2. The centering device 91 of FIG. 3 is composed of a plurality of flexible, resilient wings attached to a distal end of the shaft of the extension catheter. Alternatively, the extension catheter may be made similar or identical to the embodiments shown in FIGS. 1 and 2. If a cuff is provided at the distal end of the extension catheter, it may be preferable to provide a second lumen through the extension catheter past the cuff. This second lumen would be used to withdraw air to provide a flow balance distally of the cuff.

Also shown in FIG. 3 is the connection 93 between the proximal end of the extension catheter and the canister 22. The proximal end of the extension catheter includes a suitably sized annular orifice that mates with and actuates the closure valve located in the nozzle of the canister 22. Pulses of propellant and medicine can be delivered through the extension catheter from the canister 22 by depressing the proximal end of the extension catheter toward the canister.

Figure 4:
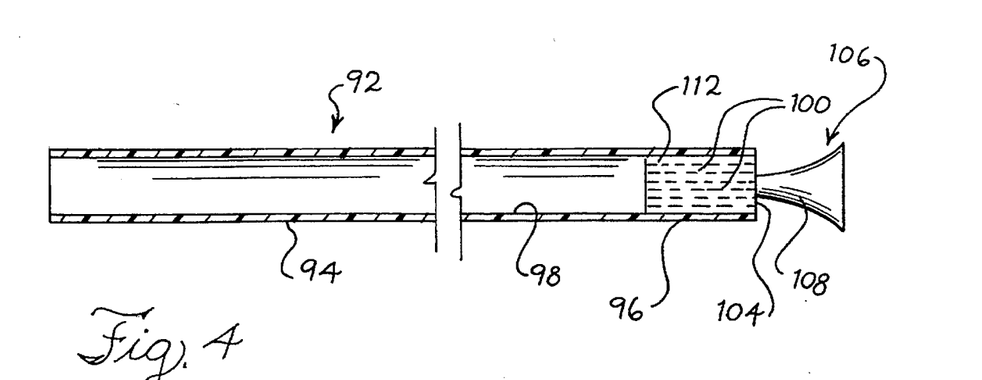
FIG. 4 is a sectional view of a distal portion of the extension catheter shown in FIGS. 1–3.
Figure 5:
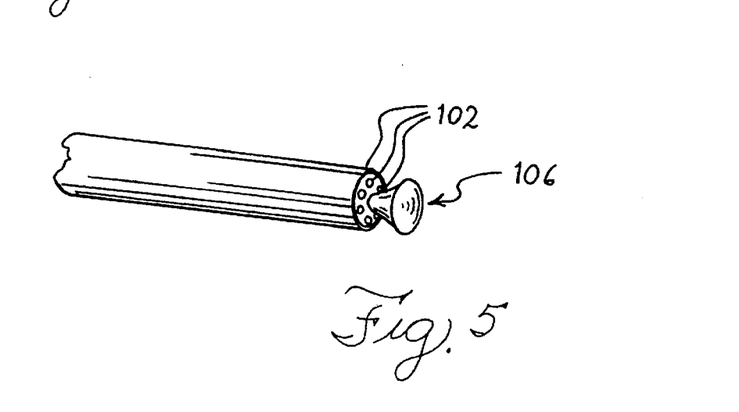
FIG. 5 is a perspective view of the embodiment shown in FIG. 4.

Referring to FIGS. 4 and 5, there is depicted a distal portion of another embodiment of the present invention. FIG. 4 shows an extension catheter 92 that can be connected to a pressurized canister such as canisters 22 or 74 shown in FIGS. 1 or 2. The extension catheter 92 includes a proximal section 94 and a distal section 96. The proximal section 94 extends back to and communicates with a suitable fitting that connects to the pressurized canister as in the previously described embodiments. In the proximal section 94 of the extension catheter 92, the extension catheter has a single lumen 98. In the distal section 96, the extension catheter 92 has a plurality of lumens 100. In one embodiment, the distal section 96 has six lumens. The plurality of lumens 100 in the distal section 96 communicate with the single lumen 98 of the proximal section 94. The plurality of lumens 100 in the distal section 96 communicate with a plurality of exit orifices 102. Accordingly, the extension catheter 92 provides a flow path for an aerosol from a pressurized canister through the lumen 98 of the proximal portion 94, the lumens 100 of the distal portion 96 and out the exit orifices 102. The plurality of lumens 100 in the embodiment of FIGS. 4 and 5 provide advantages for aerosol generation by helping to produce a fine aerosol spray and by breaking up larger particles of the medicine.

The shape of the aerosol plume can be a significant factor affecting the rate and efficacy of the delivery of medication. In general, it is preferable to generate an aerosol that has a shape that minimizes particle impaction near the distal tip of the extension catheter, given the location of the tip and the airflow conditions around it. For example, if the aerosol plume is wide, a portion of the drug may be wasted in the end of the endotracheal tube or on the tracheal wall. On the other hand, if the plume is too narrow or the velocity too high, a portion of the medicine may impact excessively on the patient's carina. In general, a low aerosol particle velocity is desirable. One of the reasons for this is to avoid impacting the carina with the discharge of a high velocity aerosol particles. In addition, it is also generally desirable to have as wide a nebulate plume as possible while avoiding significant impact with the walls of either the endotracheal tube or the airway passage. The effect of aerosol particle velocity and geometry is related to anatomical factors. In some circumstances, e.g. away from the carina, a narrow, fast nebulate plume may be preferable to a slower, wider plume.

Referring again to FIG. 5, in a preferred embodiment, the exit orifices 102 define an annular exit configuration around a periphery of a distal end of the extension catheter. Connected to the distal end 104 of the extension catheter 92 is a baffle 106. Preferably, the baffle 106 is connected to the distal end 104 at an axially concentric location centrally positioned with respect to the annular configuration of the peripheral exit orifices 102. In the embodiment shown in FIGS. 4 and 5, the baffle 106 has a horn-like shape with a narrow stem portion 108 connected at its proximal end to the distal end 104 of the extension catheter 92. The stem 108 has an increasing taper from its proximal end to its distal end thereby defining a tapered proximal face that is oriented toward the exit orifices 102. In the embodiment of FIGS. 4 and 5, the face of the baffle stem 108 is concave. The baffle 106 helps to break up by impaction any larger particles that may form at the orifices 102. The concave shape of the baffle stem 108 serves to divert the flow of aerosol from the exit orifices 102 outward from an axial direction. This has the effect of slowing down the forward velocity of the aerosol thereby enhancing entrainment in the patient's inspiratory flow. By diverting the flow of aerosol from an axial direction, the baffle serves to reduce the portion of aerosol that impinges on the carina. The baffle face should be relatively smooth to minimize collection of any drug residue. The baffle may be connected to the distal end of the extension catheter 92 by providing the distal multi-lumen portion of the catheter with a centrally located lumen and bonding a proximal end of the baffle stem 108 into the centrally located lumen.

In one embodiment, the distal section 96 of the extension catheter 92 has a length of approximately 3 mm and the proximal section 94 constitutes the remaining length of the extension catheter. The extension catheter 92 that has an overall length of approximately 35 cm. As mentioned above, the catheter shaft may have a relatively uniform, non-tapered profile, or may have a short taper near the distal tip. In this embodiment, the extension catheter 92 has an O.D. of 0.045 inches. The proximal section 94 of the extension catheter has an I.D. of 0.030 inches. In the distal section 96, each of the plurality of lumens has an I.D. of 0.005–0.007 inches. The baffle 106 has a length of 0.5 cm and tapers from a diameter of 0.010 to 0.045 inches. In the embodiment shown in FIG. 3, the multi-lumen section 96 is formed by inserting and fastening a multi-lumen plug 112 into the single lumen 98 of a catheter shaft. The plug may be made of a suitable plastic material such as polyethylene, Teflon, or nylon. The baffle may be molded as part of the plug or tip.

Figure 6:
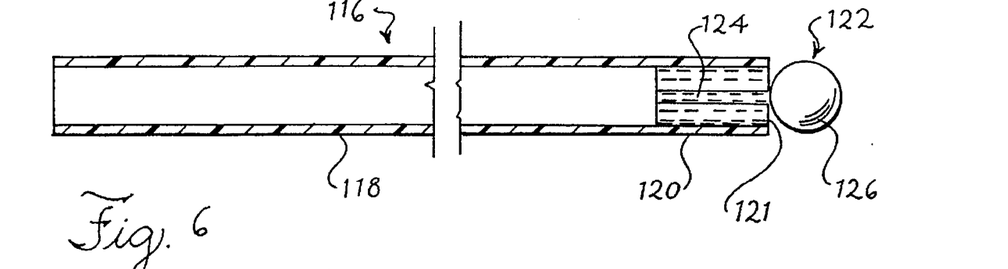
FIG. 6 is an alternative embodiment of the embodiment shown in FIG. 4
Figures 7, 8:
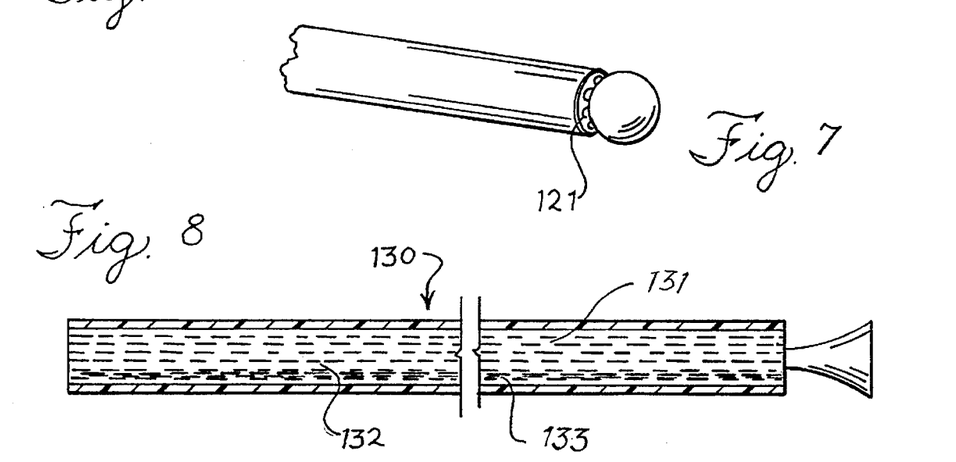
FIG. 7 is a perspective view of the embodiment shown in FIG. 6.
FIG. 8 is an alternative embodiment of the extension catheter of FIG. 4.

Referring to FIGS. 6 and 7, there is another embodiment of the present invention. Like FIG. 4, FIG. 6 shows a view of a catheter extension 116 for use with a pressured canister of medicine and liquid propellant. Like the embodiment of FIG. 4, the embodiment of the catheter extension 116 in FIG. 6 includes a single lumen proximal portion 118 and a multiple lumen distal portion 120 terminating in a plurality of annularly arranged exit orifices 121. A baffle 122 is located adjacent to the exit orifices 121. In this embodiment, the baffle 122 has a convex shape and preferably the baffle 122 is spherical. The baffle 122 includes a proximal stem 124 and a ball-shaped baffle portion 126. The stem 124 connects to the distal end of the catheter extension and in particular, the stem is bonded into a centrally located lumen that extends through the multi-lumen distal portion. The spherical baffle 126 has a diameter corresponding approximately to the O.D. of the catheter extension 116. The spherical baffle 126 is at, or close to, the distal end of the catheter extension 116. The baffle 126 helps to break up by impaction any large particles that may form at the orifices 121. In addition, the spherical baffle 126 serves to reduce the forward velocity of the aerosol from the exit orifices by causing a foil-effect. Also, the spherical baffle 126 also serves to divert the flow of aerosol away from the carina. The spherical baffle 126 may be composed of a suitably smooth material, such as a plastic or metal.

FIG. 8 shows an alternative embodiment of an extension catheter 130. The embodiment of the extension catheter 130 shown in FIG. 8 is similar to that of FIGS. 4 and 5 except that instead of having a proximal single lumen section and a distal multi-lumen section, the embodiment of FIG. 8 has a multi-lumen section 132 through the entire length of the catheter 130. The catheter 130 has a shaft which may be formed as a multi-lumen extrusion of a single plastic material. The dimensions of the multiple lumens and the baffle would be similar to that of FIGS. 4 and 5. An advantage of the embodiment of FIG. 8 relates to manufacturing efficiency. In addition, a centering device, similar to the device shown in FIGS. 1–3 may extend from the baffle.

Figure 9:
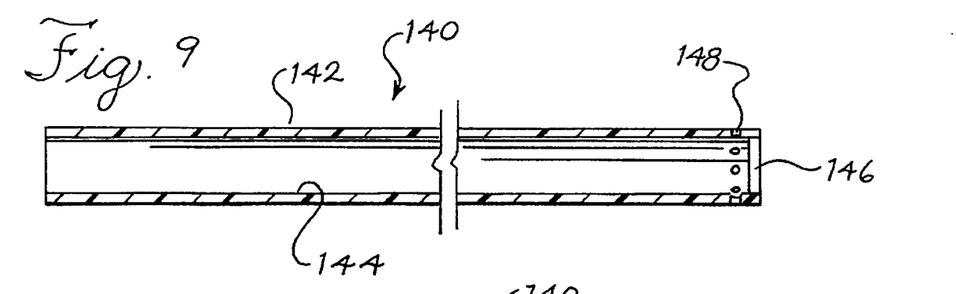
FIG. 9 is another alternative embodiment of the extension catheter of FIG. 4.
Figure 10:
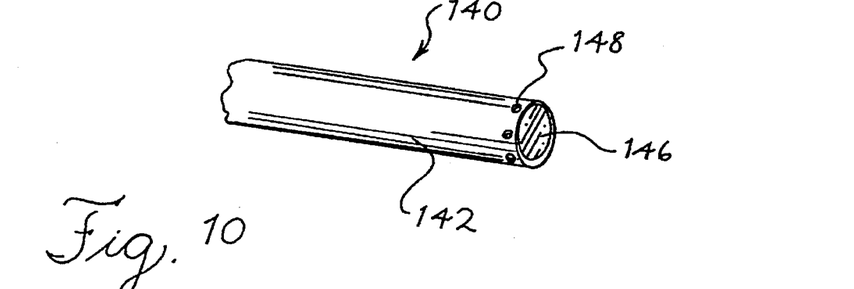
FIG. 10 is a perspective view of the embodiment shown in FIG. 9.

As mentioned above, in order to improve the delivery rate of a medicine delivered as an aerosol, it may be preferable to reduce the velocity of the aerosol as much as possible so that it can be entrained by the inspiratory airflow. The embodiment of the present invention shown in FIGS. 9 and 10 is directed to delivering an aerosol from a pressurized canister containing a mixture of a medicine and a liquid propellant and to reduce the forward velocity of the aerosol as it is expelled from the end of the catheter. In FIG. 9, an extension catheter 140 has a shaft 142. The proximal end (not shown) of the extension catheter 140 connects to a pressurized canister and is used as shown in FIGS 1–3. The shaft 142 of the catheter 140 has a single lumen 144, however alternatively, it may also be provided with a multi-lumen construction as shown in FIG. 8 or a single and multiple lumen construction as in FIGS. 4 and 5. Located at a distal end of the lumen 144 is a plug 146. The plug 146 completely occludes the end of the lumen 144. A plurality of exit orifices 148 are located through a wall of the shaft 142 immediately proximal of the plug 146. The exit orifices 148 are oriented in a radial direction. In a preferred embodiment, there are 6 exit orifices each having a diameter of 0.005 inches. The size and orientation of the exit orifices serve to direct the generated aerosol from the catheter extension in a radial direction thereby reducing the forward velocity of the aerosol particles so that they become entrained in the inhalation airflow. The plug 146 may be formed of a suitable plastic material, such as polyethylene, nylon or Teflon, and bonded to the shaft by heat sealing or a suitable adhesive. Alternatively, the plug may be formed by heat sealing the tip. The multiple orifices may be formed by drilling through the wall of the catheter shaft, by using multiple mandrels, or by forming the tip as a molded component. The orifices may be adjusted to suit the aerosol.

Figure 11:
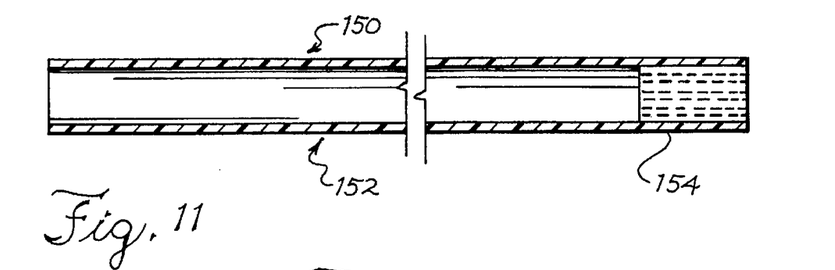
FIG. 11 is a sectional view of a distal portion of another alternative embodiment of the extension catheter of FIG. 4.
Figure 12:
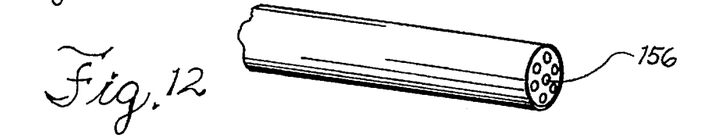
FIG. 12 is a perspective view of the embodiment of FIG. 11.
Figure 13:
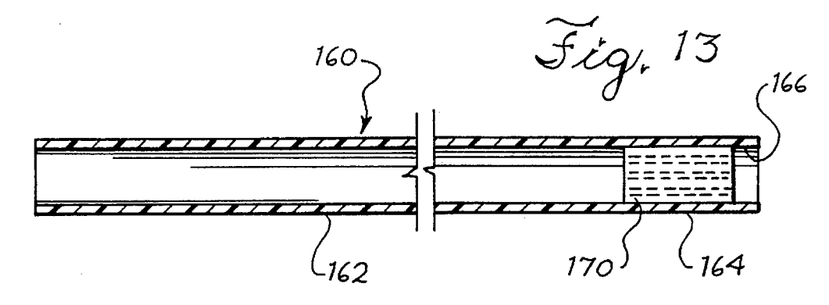
FIG. 13 is a sectional view of a distal portion of yet another alternative embodiment of the extension catheter of FIG. 4.
Figure 14:
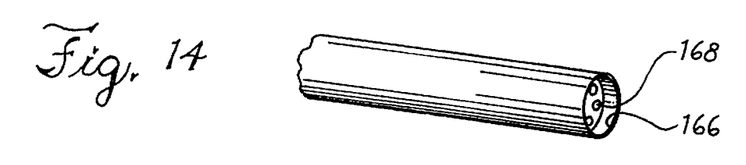
FIG. 14 is a perspective view of the embodiment of FIG. 11.
Figure 15:
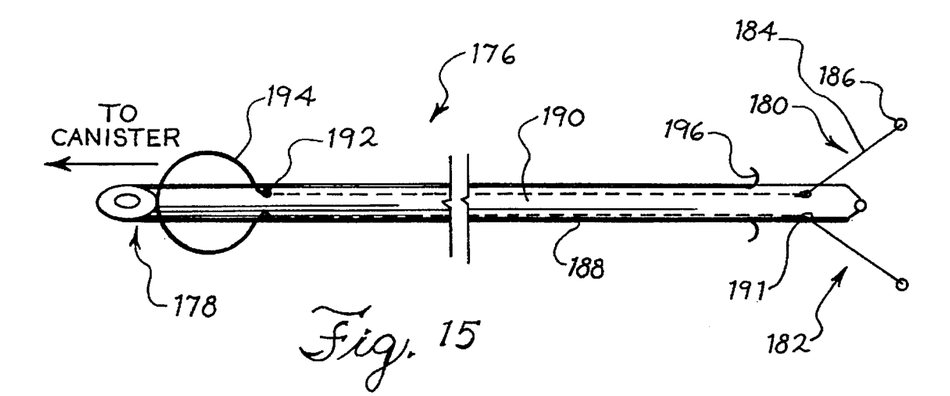
FIG. 15 is a side view of another embodiment of the extension catheter shown in FIG. 1.
Figure 16:
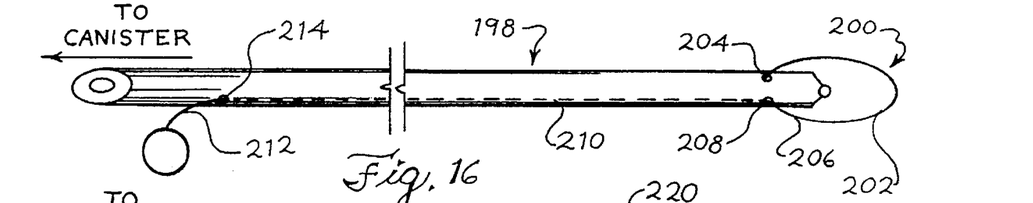
FIG. 16 is a side view of another embodiment of the extension catheter of FIG. 15.
Figure 17:
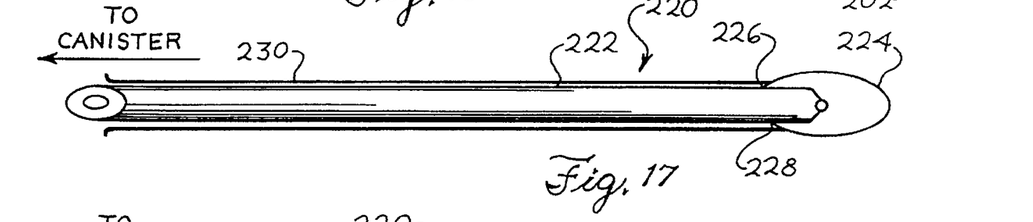
FIG. 17 is a side view of another embodiment of the extension catheter of FIG. 15.
Figure 18:
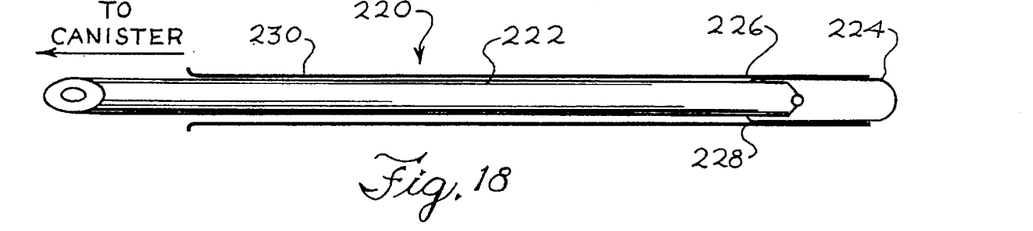
FIG. 18 is a side view of the embodiment of FIG. 17 with the outer sheath advanced over the centering device for installation or withdrawal.

FIGS. 11 and 12 show another embodiment of the present invention. An extension catheter 150 has a single lumen proximal section 152 and a multiple lumen distal section 154 similar to that of FIGS. 4 and 5. Unlike the embodiment of the extension catheter in FIGS. 4 and 5, the extension catheter 150 in FIGS. 11 and 12 does not include a distal baffle. The lumen 156 which otherwise may be used for connection of the baffle may be used as an aerosol exit orifice instead. In other respects, the embodiment of the extension catheter 150 is similar to that of FIGS. 4 and 5. The embodiment of FIGS. 11 and 12 may be used when a baffling effect is considered unnecessary.

FIGS. 13 and 14 show another embodiment of the present invention. An extension catheter 160 has a single lumen proximal section 162 and a multiple lumen distal section 164 similar to that of FIGS. 11 and 12. Unlike the previous embodiment, the extension catheter 160 has a tubular extension 166 that extends distally past the exit orifices 168. The tubular extension 166 serves to protect the exit orifices 168 during positioning and placement. In addition, since the cross section of the tubular extension 166 is greater than the combined cross section of the multiple lumens of the distal section, it serves to reduce the velocity of the aerosol as it is generated at the distal end of the extension catheter 160. The tubular extension 166 may be formed by positioning a plug 170 that forms the multiple lumen distal section 164 slightly back from the distal end of the tubular shaft used to form the body of the extension catheter 160. Alternatively, the tubular extension 166 may be formed by attaching a separate tube of material onto the distal end of the catheter shaft. In one embodiment, the tubular extension 166 is approximately 2–7 mm in length. The tubular extension 166 may be uniform or may be flared. The multiple orifices may be formed by drilling through the plug, by using multiple mandrels in a molding process, or by a molding process.

FIG. 15 shows an alternative embodiment of the extension catheter. An extension catheter 176 is used in conjunction with a pressurized canister as described above. The extension catheter 176 has a proximal end 178 with a suitable fitting for connecting to a pressurized medicine/propellant canister (not shown) and a distal end 180 that can be placed deep within a patient's respiratory tract and from which an aerosol from the pressurized medicine/propellant canister can be discharged. The extension catheter 176 includes a centering device 182. The centering device 182 includes a plurality of arms 184 that are formed to resiliently extend outward from the axis of the extension catheter shaft to engage the wall of the patient's trachea or airway passage or the interior of an endotracheal tube depending upon the location of the distal end of the extension catheter. At the ends of each of the arms 184 are balls 186. The proximal ends of the arms 184 are formed of wires 188 that extend through lumens 190 in the shaft of the extension catheter 176. Each of the lumens 190 has a distal opening 191 from which an arm can extend. The distal openings are approximately 0.10–1 cm from the distal end of the catheter shaft. The proximal ends of the wires 188 exit the lumens 190 of the shaft of the extension catheter via openings 192 that are close to the proximal end 178 of the extension catheter in a portion of the extension catheter 176 that would normally be outside the patient's body during use. Thus, the proximal ends 194 of the wires 188 are accessible to the physician during use. By pulling and pushing on the proximal ends 194 of the wires 188, the portion of the arms 184 that extend from the openings 191 can be adjusted. Thus, the arms 184 can be adjusted from a fully retracted to a fully advanced position by pulling or pushing on the proximal ends 194 of the wires 188. In addition, since the proximal ends 194 can be adjusted in any intermediate position between the fully retracted and fully advanced positions, a physician can adjust the size of the centering device 180 to any appropriate size, as desired. Thus, the size of the centering device can be adjusted to different sizes of airway passages for use in different patients or alternatively the size of the arms can be adjusted to different airway passages in the same patient if the physician desires to relocate the extension catheter to different locations in a patient's respiratory tract. In a present embodiment, the arms are formed of a suitable resilient, flexible material such as nitinol, stainless steel or plastic.

In one embodiment, a second centering device 196 is also provided. The second centering device 196 is located on the shaft of the extension catheter 176 proximally from the first centering device 180. In a present embodiment, the two centering devices are approximately 0.5 to 3 inches apart. The second centering device 196 may be formed of resilient wings formed of a material such as plastic or metal that extend radially outward from the shaft. The second (or proximal) centering device 196 helps keep the distal portion of the extension catheter 176 in alignment.

FIG. 16 shows another alternative embodiment of the present invention. An extension catheter 198 is shown which may be used similarly to the extension catheter 30 of FIG. 1. The extension catheter 198 includes a centering device 200. The centering device 200 includes a wire loop 202 located at a distal end of the extension catheter 198. One end 204 of the loop 202 connects to the distal end of the extension catheter shaft. The other end 206 of the wire loop 202 enters an opening 208 in the shaft that communicates with a lumen 210 that extends to a proximal end of the extension catheter 198. A proximal end 212 of the wire exits the lumen 210 via an opening 214 in a proximal portion of the extension catheter which is normally outside the patient's body during use. The size of the wire loop 202 can be adjusted by advancing or withdrawing the proximal end 212 of the wire. When in an expanded size, the wire loop 202 engages the walls of the trachea or airway passage or the interior of the endotracheal tube depending upon where the distal end of the extension catheter is positioned. The size of the wire loop 202 can be adjusted from a fully reduced size to a fully expanded size as well as intermediate sizes. In a one embodiment, more than one wire loop may be provided at the distal end of the extension catheter 198.

FIGS. 17 and 18 show another alternative embodiment of the present invention. An extension catheter 220 has a shaft portion 222 and a wire loop 224 extending from a distal end of the shaft 222. In this embodiment, the wire loop 224 is connected at each end 226 and 228 to the distal end of the catheter shaft 222. A retractable sheath 230 is positioned over the extension catheter shaft 222. The sheath 230 can be advanced and withdrawn relative to the extension catheter shaft 222. When it is desired to maneuver the extension catheter into a desired position in the respiratory tract of a patient, the sheath 230 is advanced over the loop 224 to maintain a low profile, as shown in FIG. 18. When the distal end of the extension catheter is suitably positioned, the sheath 230 is then retracted, as shown in FIG. 17, allowing the loop 224 to expand to its expanded size to center and align the distal end of the extension catheter 220 in the respiratory tract. The sheath 230 may be provided only for this function or alternatively, the sheath 230 may also be provided by a catheter that provides an additional function in the respiratory tract, such as a suction catheter. In addition, the sheath 230 may also be used to clean or wash the extension catheter when it is withdrawn in a similar manner as a suction catheter is cleaned.

Figure 19:
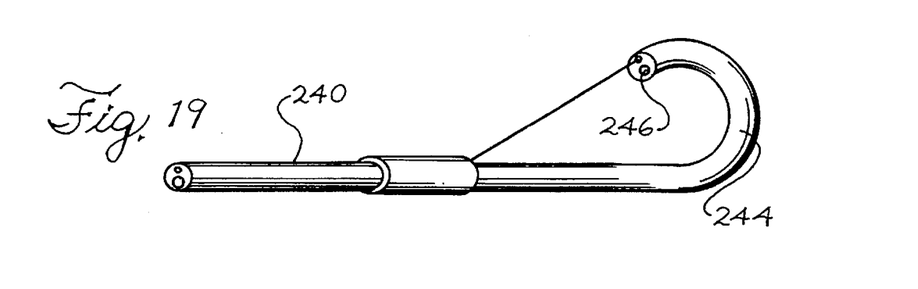
FIG. 19 is a side view of an alternative embodiment of the extension catheter of FIG. 1.
Figure 20:
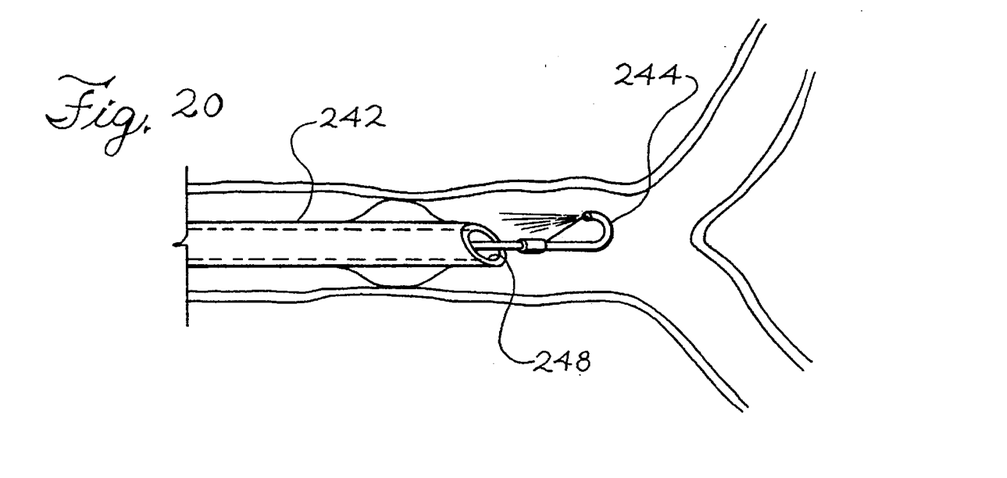
FIG. 20 is a view of the embodiment of FIG. 19 shown in place in a trachea of a patient.

Referring to FIGS. 19 and 20, there is an alternative embodiment that utilizes a counterflow catheter arrangement. FIG. 20 shows an extension catheter 240 located inside of an endotracheal tube 242. A proximal end of the extension catheter 240 extends back and communicates with a suitable fitting that connects to a pressurized canister as in the previously described embodiments. The extension catheter 240 extends distally of the endotracheal tube 242 and has a distal section 244 that curves back on itself. The extension catheter 240 has one or more distal orifices 246 that deliver a plume of aerosol particles in a reverse, i.e. proximal, direction back toward the distal opening 248 of the endotracheal tube 242. In order to maintain a proper reverse orientation and to prevent snagging, the extension catheter 240 includes a wire 250 that extends from the distal tip of the extension catheter 240. The wire 250 is secured on the catheter near the tip. The wire 250 can be secured by doubling back the end of the wire and imbedding it into the catheter shaft. A heat shrunk tube 252 located on the shaft of the extension catheter may be used to secure the end of the wire 250.

In the embodiment shown in FIGS. 19 and 20, the extension catheter 240 directs an aerosol plume in a reverse direction back toward the distal opening 248 of the endotracheal tube 242. The plume from the extension catheter encounters the flow of air from the endotracheal tube 242 during the inhalation phase of the patient. The inhalation of air through the endotracheal tube 242 causes the aerosol to reverse direction and carries it to the lungs. Reversal of direction of the aerosol has the effect of minimizing the particle velocity and may increase the distance travelled by the particles allowing more opportunity for the propellant to flash off with a resultant decrease in the size of the particles.

Although the embodiments of the invention have been described in terms of their utility in connection with a canister similar to those used in conjunction with a metered dose inhaler, the embodiments of the present invention could also be used in conjunction with any pressurized canister device, even those that are non-metered. This includes systems or arrangements in which a medicine in liquid form is delivered under pressure to a distal end of a catheter and merely sprayed from the distal end. The embodiments of the present invention could also be used with other means of supplying a drug-propellant mixture, especially when a bolus-metering or timing device is incorporated into the catheter system. This would include dry powder aerosol delivery system.

The embodiments of the extension catheter system used with a pressurized canister may also be modified to incorporate additional features or functions. These additional features may serve either therapeutic or diagnostic purposes or may assist in the use, placement or operation of the extension catheter system. For example, the extension catheter may include a separate fiber optical viewing means incorporated into the extension catheter. For example, an optical fiber viewing means 133 may be located one of the lumens of the multi-lumen embodiment 130 of FIG. 8. Also, the extension catheter may include one or more sensors or lumens for measuring physiological parameters of the patient. For example, one of the lumens, such as lumen 131 in FIG. 8, may be used for measuring a physiological parameter of the patient. In addition, the extension catheter may be used with a separate guide wire which is removable or non-removable to assist in positioning the extension catheter into the desired airway passage.

A device into which an extension catheter can be adapted is a suction or aspiration catheter. A suction catheter is sometimes used in conjunction with an endotracheal tube to aspirate mucous secretions out of a patient's respiratory system. A conventional suction catheter is inserted down the ventilation lumen of the endotracheal tube and out the distal end. A mucolytic agent may be administered via a lumen of the suction catheter to help in the withdrawal of mucous from the trachea or bronchi. The suction catheter may then be withdrawn from the endotracheal tube and either disposed or retained in a sterile sheath connected to a proximal end of the endotracheal tube so that it can be reinserted into the endotracheal tube again.

An extension catheter, similar to any of the embodiments described above, can be incorporated into a suction catheter so that a single device can perform both the functions of aspiration and aerosol delivery. Embodiments of a suction catheter combined with a extension catheter are shown catheter is FIGS. 21–28. FIGS. 21–25 show a suction catheter assembly 300. The suction catheter assembly 300 includes a suction catheter shaft 302 slidably located inside of a flexible sheath 304. A suction lumen 305 extends through the suction catheter shaft 302. A proximal manifold 306 includes a port 308 for connecting a vacuum source to the suction lumen 305. A valve 310 operates to open and close the port 308. A distal manifold 312 provides for connecting to an endotracheal tube such that the suction catheter shaft 302 can be inserted into the endotracheal tube by pushing the proximal manifold 306 toward the distal manifold 312. A distal seal 313 is located in the distal manifold 312 and serves to clean the shaft 302 of the suction catheter as it is slidably withdrawn through the manifold 312 into the sheath 304.

Figures 21, 22:
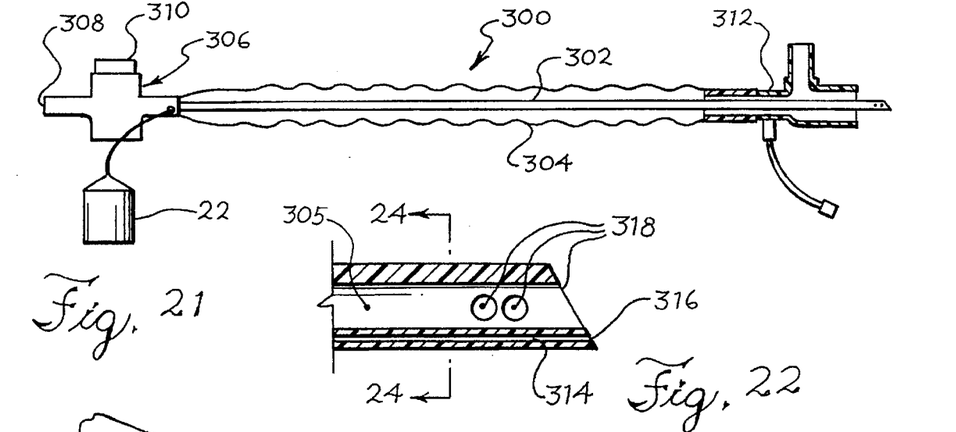
FIG. 21 is a perspective view of an embodiment of the extension catheter incorporated into a suction catheter.
FIG. 22 is a sectional view of the distal end of the suction catheter of FIG. 21.

The suction catheter assembly 300 includes an additional lumen 314. This lumen 314 is located in a wall of the suction catheter shaft 302. This lumen 314 communicates with a distal orifice 316 located at a distal end of the suction catheter shaft 302. This lumen 314 is used to deliver a mixture of medicine and liquid propellant from a pressured canister 22, as described above. Also located at a distal end of the suction catheter shaft 302 are suction openings 318.

The suction catheter assembly 300 can be used in a conventional manner to remove mucous from the trachea and from the bronchi. The suction catheter assembly 300 can also be used to deliver medicines to the lungs as an aerosol by means of the lumen 314. The lumen 314 can also be used to deliver mucolytic agents as an aerosol provided that mucolytic agents are available in pressurized canister form. Because the aerosol delivered by the lumen 314 can be carried by a patient's inspiratory airflow into the bronchi, the mucolytic agent can be delivered further into bronchi compared to a suction catheter that merely instills a mucolytic agent.

Figure 23:
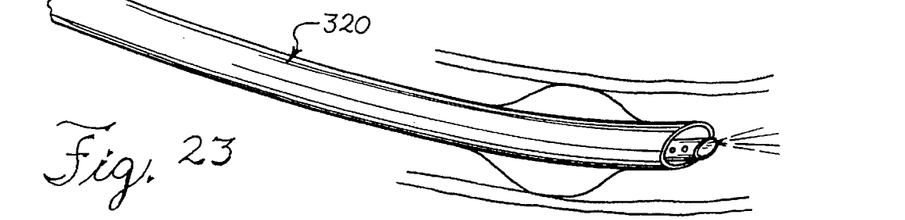
FIG. 23 is a perspective view of the embodiment of FIG. 21 used in conjunction with an endotracheal tube inside a patient's respiratory tract.
Figure 24:
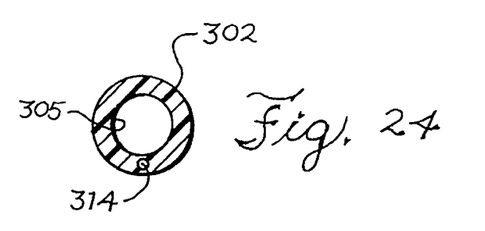
FIG. 24 is a cross sectional view of the embodiment of FIG. 22 taken along lines a–a'.
Figure 25:
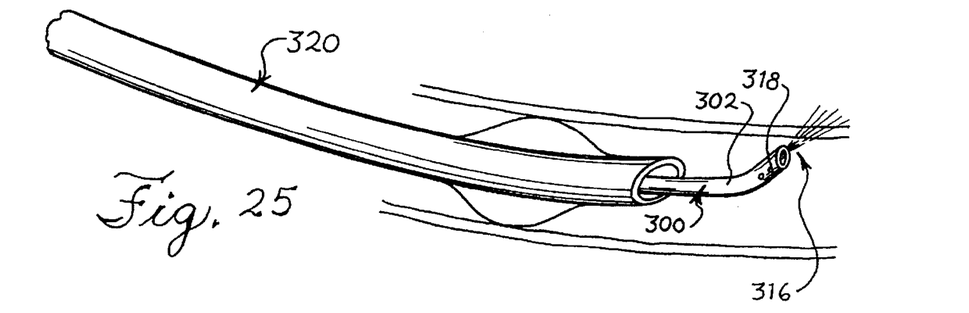
FIG. 25 is a perspective view similar to FIG. 24 showing the suction catheter in another stage of operation.

When using the suction catheter assembly 300, it can be positioned so that a distal end of the suction catheter shaft 302 is close to the distal end of the endotracheal tube 320 as shown in FIG. 23 or alternatively the suction catheter shaft 302 can be positioned so that it extends past the distal end of the endotracheal tube 320 as shown in FIG. 25. As shown in FIG. 25, the suction catheter shaft 302 may be formed with a distal curvature so that the distal end can be brought into proximity with the tracheal wall.

Rather than incorporate the lumen 314 into the wall of the suction catheter, it may be preferably in many situations to use a conventional suction catheter with a stand-alone extension catheter. The stand-alone extension catheter may be similar to any of the embodiments described above. A suction catheter and an extension catheter can readily be used together with the alternative versions of the manifolds shown in FIGS. 26–28.

Figure 26:
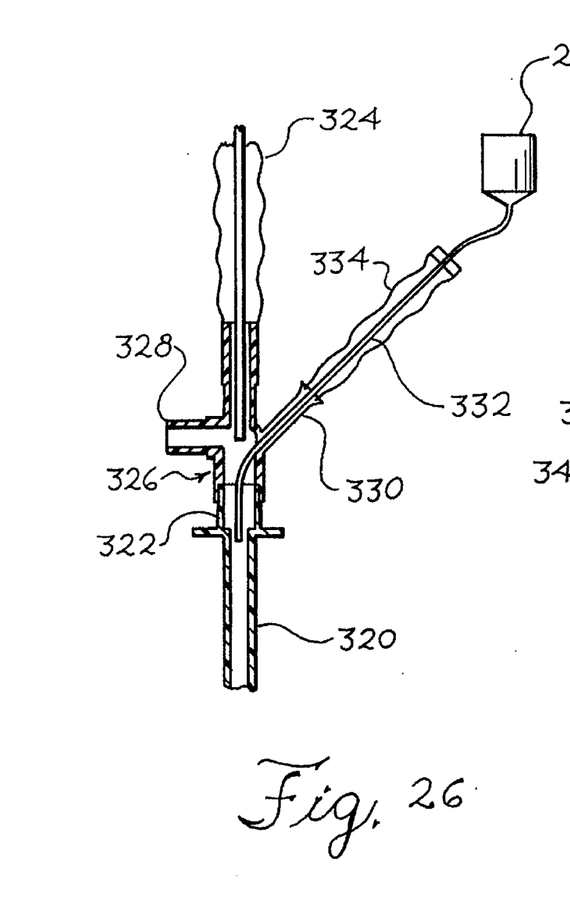
FIG. 26 is a sectional view of one embodiment of a connection arrangement between an endotracheal tube, a suction catheter and an extension catheter.

Referring to FIG. 26, an endotracheal tube 320 has a proximal end with a single port 322. A suction catheter 324 has a distal manifold 326. The suction catheter manifold 326 connects to the single port 322 of the endotracheal tube 320. The manifold 326 has a first port 328 for connecting to a ventilator and a second port 330 for connecting to a proximal end of a extension catheter 332. (As shown in FIG. 26, the extension catheter 332 includes a sterile sheath 334 which is similar to the sheath included on the suction catheter 324. In the embodiment of FIG. 26, the suction catheter 324 and the extension catheter 332 are positioned alternately inside the ventilation lumen of the endotracheal tube 320. The suction catheter or the extension catheter can be withdrawn temporarily and maintained in its sterile sheath while the other is being used.

Figure 27:
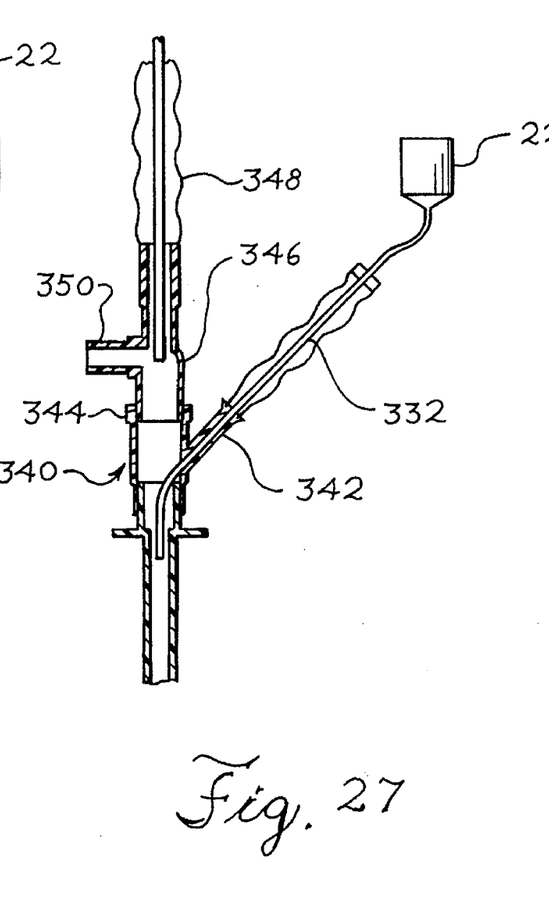
FIG. 27 is a sectional view similar to FIG. 26 showing another embodiment of an arrangement for connecting an endotracheal tube, a suction catheter and an extension catheter.

Referring to FIG. 27 there is another arrangement for connecting a suction catheter and extension catheter to an endotracheal tube. In this embodiment, a manifold 340 connects to the proximal end of the endotracheal tube 320. The manifold 340 port 342 for receiving the extension catheter 332 and a second port 344. A distal manifold 346 of a suction catheter 348 connects to the second port 344. The suction catheter manifold 346 has a port 350 for connecting to the ventilator. This arrangement can be used similarly to the arrangement of FIG. 26.

Figure 28:
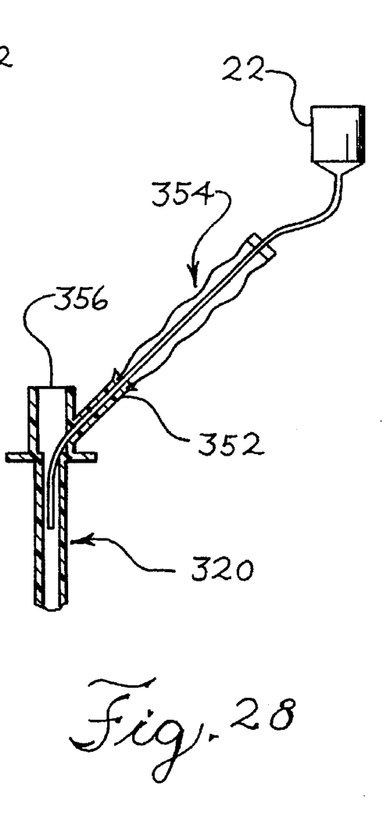
FIG. 28 is a sectional view similar to FIG. 26 showing another alternative arrangement for connecting an endotracheal tube and an extension catheter.

FIG. 28 shows still another arrangement for connecting a suction catheter and a extension catheter to an endotracheal tube. In this embodiment, the endotracheal tube 320 is provided with a proximal end that includes dual ports. A first port 352 receives the extension catheter 354. The second port 356 may be connected to either directly to a ventilator or may be connected to a distal end of a suction catheter (not shown) in a conventional manner.

Regarding the embodiments described above, certain of the embodiments may be preferable from the standpoint of versatility, i.e. they may be able to deliver a variety of medications having different viscosities, suspensions, surface tensions, etc. Others of the embodiments may be more suitable for the delivery of specific types of medications or the delivery of particles of certain sizes.

It is intended that the foregoing detailed description be regarded as illustrative rather than limiting and that it is understood that the following claims including all equivalents are intended to define the scope of the invention.

I claim:

1. An improved system for the delivery of an aerosolized medicine to a patient's respiratory system comprising:

a pressurized canister that contains a mixture of fine particles of a medicine and a propellant in a liquid state and further that has an outlet from which the medicine and propellant can exit the canister;

an endotracheal tube having a ventilation lumen;

an extension catheter having a proximal end and a distal end and a lumen extending from the proximal end to a distal orifice located at said distal end, said extension catheter located in said ventilation lumen of said endotracheal tube, and extending distally of a distal end of said endotracheal tube into an air flow passage of the patient; and a connection between said proximal end of said extension catheter and said outlet of said pressurized canister to provide a fluid connection between said canister and said lumen of said extension catheter to permit liquid medicine and propellant to be conveyed from said canister through said lumen of said extension catheter and out said distal orifice of said extension catheter where the propellant evaporates and an aerosol of the liquid medical agent is generated.

2. The system of claim 1 in which said extension catheter is removable with respect to said endotracheal tube.

3. The system of claim 1 further comprising:

a first centering device associated with a distal portion of said extension catheter to align said distal end of said catheter with respect the patient's air flow passage.

4. The system of claim 3 further comprising:

a second centering device associated with said distal portion of said extension catheter to align said distal end of said extension catheter with respect the patient's air flow passage.

5. The improved system of claim 1 further comprising:

means for sensing a physiological condition of the patient incorporated into said extension catheter.

6. The improved system of claim 1 in which said extension catheter further comprises:

a separate fiber optical viewing means.

7. The improved system of claim 1 further comprising:

means for synchronizing production of the aerosol with inhalation of the patient.

8. The improved system of claim 7 in which said synchronizing means further comprises:

means for producing the aerosol in advance of the inhalation of the patient.

9. An apparatus for delivery of an aerosolized medicine to a patient's respiratory tract comprising:

a pressurized canister containing a mixture of fine particles of a medicine and a liquid propellant and further in which an aerosolized dose of the medicine can be generated when the mixture is expelled to ambient pressure at which the propellant in the mixture evaporates;

a catheter having a lumen extending therethrough and a length such that a proximal end of said catheter is located outside the patient's body and a distal end is located in an air flow passage in the patient's respiratory tract, said distal end having an exit orifice communicating with said lumen;

a proximal portion of said catheter and said canister having a permanent connection to each other so as to permit the mixture from said canister to be transmitted into the lumen of said catheter; and an actuator valve located in at least one of said catheter and said canister to regulate the flow of mixture from said canister to said exit orifice.

10. An apparatus for delivery of an aerosolized medicine to a patient's respiratory tract from a pressurized canister of a type that contains a mixture of fine particles of a medicine and a liquid propellant and further in which an aerosolized dose of the medicine is generated when the mixture is expelled to ambient pressure at which the propellant in the mixture evaporates, said apparatus comprising:

a catheter having a lumen extending therethrough and a length such that a proximal end of said catheter is located outside the patient's body and a distal end is located in an air flow passage in the patient's respiratory tract, said distal end having an exit orifice communicating with said lumen;

a connection between a proximal portion of said catheter and said canister to permit the mixture from said canister to be transmitted into the lumen of said catheter, said lumen and said exit orifice sized to maintain a pressure inside said lumen sufficient to maintain said mixture in a liquid state; and a baffle located adjacent to said exit orifice.

11. The apparatus of claim 10 in which said exit orifice has an annular configuration, and in which said baffle further comprises:

a stem portion connected to said distal end of said catheter concentric with said annular configuration of said exit orifice.

12. The apparatus of claim 10 in which said baffle further comprises:

a proximal face located directly in front of said orifice.

13. The apparatus of claim 12 in which said proximal face defines a tapered surface increasing in diameter in a distal direction.

14. The apparatus of claim 13 in which said tapered surface is defines a concave curved surface.

15. The apparatus of claim 13 in which said tapered surface is defines a convex curved surface.

16. The apparatus of claim 15 in which said convex curved surface is spherical.

17. The apparatus of claim 10 in which said distal exit orifice has an annular configuration.

18. An apparatus for the delivery to a patient's respiratory tract of an aerosolized medicine from a pressurized canister containing a mixture of a medicine and a liquid propellant that evaporates upon exiting to ambient pressure to generate an aerosolized dose of said medicine, said apparatus comprising:

a catheter having a shaft with a length such that a proximal end of said catheter is located outside the patient's body and a distal end is located in an air flow passage in the patient's respiratory tract, wherein at least of portion of said shaft has a plurality of parallel lumens extending therethrough; and a connection between a proximal portion of said catheter and an outlet of a canister to permit the mixture of medicine and propellant from said canister to be transmitted through said plurality of parallel lumens and out at least one exit orifice located at the distal end of said catheter.

19. The apparatus of claim 18 in which said plurality of lumens terminate in a plurality of exit orifices located at the distal end of said catheter.

20. The apparatus of claim 19 further comprising:

a baffle located adjacent to said exit orifices.

21. The apparatus of claim 18 in which said plurality of lumens extend from a proximal to a distal end of said catheter shaft.

22. The apparatus of claim 21 in which the catheter shaft is formed of a multi-lumen extrusion.

23. The apparatus of claim 18 in which said catheter shaft comprises a portion having a single lumen, said single lumen communicating with said plurality of lumens.

24. The apparatus of claim 18 further comprising:

an insert plug located in a lumen of said catheter shaft, said insert plug having a plurality of lumens extending therethrough that define said plurality of lumens.

25. The apparatus of claim 18 further comprising:

a centering device associated with a distal portion of said catheter to align said distal end of said catheter with respect the air flow passage in a patient's respiratory tract.

26. An apparatus for the delivery to a patient's respiratory tract of an aerosolized medicine from a pressurized canister containing a mixture of a medicine and a liquid propellant that evaporates upon exiting to ambient pressure to generate an aerosolized dose of said medicine, said apparatus comprising:

a catheter having a shaft with a length such that a proximal end of said catheter is located outside the patient's body and a distal end is located in an air flow passage in the patient's respiratory tract, said catheter shaft having at least one lumen extending from said proximal end to said distal end, and further in which said catheter shaft includes a plurality of exit orifices located at said distal end, said distal exit orifices communicating with said at least one lumen; and a connection between a proximal portion of said catheter and an outlet of said canister to permit the mixture of medicine and propellant from said canister to be transmitted through said at least one lumen and out said plurality of exit orifices.

* * * * *

UNITED STATES PATENT AND TRADEMARK OFFICE
CERTIFICATE OF CORRECTION

PATENT NO. : 5,642,730
DATED : July 1, 1997
INVENTOR(S) : Baran

It is certified that error appears in the above-indentified patent and that said Letters Patent is hereby corrected as shown below:

In claim 3, Column 18, line 13, after "respect" please insert -- to --.

In claim 4, Column 18, line 18, after "respect" please insert -- to --.

In claim 14, Column 19, line 21, delete "is".

In claim15, Column 19, line 23, delete "is".

In claim 25, Column 20, line 21, after "respect" insert -- to --.

Signed and Sealed this

Twelfth Day of December, 2000

*Attest:*

Q. TODD DICKINSON

*Attesting Officer*  *Director of Patents and Trademarks*